United States Patent
Kim et al.

(10) Patent No.: US 10,438,363 B2
(45) Date of Patent: Oct. 8, 2019

(54) METHOD, APPARATUS AND PROGRAM FOR SELECTIVE REGISTRATION THREE-DIMENSIONAL TOOTH IMAGE DATA TO OPTICAL SCANNING TOOTH MODEL

(71) Applicant: KOREA INSTITUTE OF SCIENCE AND TECHNOLOGY, Seoul (KR)

(72) Inventors: Youngjun Kim, Seoul (KR); Hyun Chul Cho, Seoul (KR); Deukhee Lee, Seoul (KR); Laehyun Kim, Seoul (KR); Se Hyung Park, Seoul (KR); Jung-Woo Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 151 days.

(21) Appl. No.: 15/796,900

(22) Filed: Oct. 30, 2017

(65) Prior Publication Data

US 2018/0122089 A1    May 3, 2018

(30) Foreign Application Priority Data

Nov. 1, 2016    (KR) .......................... 10-2016-0144635

(51) Int. Cl.
*G06K 9/00* (2006.01)
*G06T 7/33* (2017.01)
(Continued)

(52) U.S. Cl.
CPC .............. *G06T 7/344* (2017.01); *A61B 5/055* (2013.01); *A61B 6/032* (2013.01); *A61B 6/14* (2013.01);
(Continued)

(58) Field of Classification Search
None
See application file for complete search history.

(56) References Cited

U.S. PATENT DOCUMENTS 6,582,229 B1 * 6/2003 Miller .................... A61C 11/00
433/213
8,199,988 B2 6/2012 Marshall et al.
(Continued)

FOREIGN PATENT DOCUMENTS

KR    10-2011-0114717 A    10/2011
KR       10-1252277 B1    4/2013
(Continued)

OTHER PUBLICATIONS

Frits A. Rangel et al., "Integration of Digital Dental Casts in Cone-Beam Computed Tomography Scans", ISRN dentistry, 2012, pp. 1-6, 949086.
(Continued)

*Primary Examiner* — Shervin K Nakhjavan
(74) *Attorney, Agent, or Firm* — Rabin & Berdo, P.C.

(57) ABSTRACT

A method for registering a tooth image with a tooth structure according to an embodiment includes a first registering step for registering a tooth image model obtained from a medical image taken when an object bites a bite including a marker with a bite scanning model obtained by scanning the bite, a second registering step for registering the bite scanning model with a tooth scanning model obtained by scanning a tooth shape of the object, and a third registering step for registering the tooth image model with the tooth scanning model based on the results of the first registering step and the results of the second registering step. As a result, a model including an accurate shape of tooth part difficult to obtain from a medical imaging apparatus can be easily obtained.

13 Claims, 22 Drawing Sheets

(51) Int. Cl.
  *A61B 5/055* (2006.01)
  *A61B 6/03* (2006.01)
  *A61B 6/14* (2006.01)
  *A61B 6/00* (2006.01)
  *A61C 9/00* (2006.01)
  *A61C 19/05* (2006.01)
  *A61B 5/00* (2006.01)

(52) U.S. Cl.
  CPC .......... *A61B 6/4085* (2013.01); *A61C 9/0046* (2013.01); *A61C 9/0053* (2013.01); *A61C 19/05* (2013.01); *A61B 5/4542* (2013.01); *G06T 2207/10028* (2013.01); *G06T 2207/10081* (2013.01); *G06T 2207/20104* (2013.01); *G06T 2207/30036* (2013.01); *G06T 2207/30204* (2013.01); *G06T 2210/41* (2013.01)

(56) References Cited

U.S. PATENT DOCUMENTS

| 9,421,074 | B2 | 8/2016 | Sachdeva et al. | |
|---|---|---|---|---|
| 10,111,714 | B2* | 10/2018 | Kopelman | A61C 9/0053 |
| 2003/0169913 | A1* | 9/2003 | Kopelman | A61B 6/14 |
| | | | | 382/132 |
| 2004/0015327 | A1* | 1/2004 | Sachdeva | A61C 7/00 |
| | | | | 702/167 |
| 2009/0042167 | A1* | 2/2009 | Van Der Zel | A61C 1/084 |
| | | | | 433/215 |
| 2010/0260405 | A1* | 10/2010 | Cinader, Jr. | A61C 7/00 |
| | | | | 382/131 |
| 2012/0015316 | A1* | 1/2012 | Sachdeva | G06T 17/00 |
| | | | | 433/24 |
| 2012/0214121 | A1* | 8/2012 | Greenberg | A61B 5/0088 |
| | | | | 433/24 |
| 2014/0272772 | A1* | 9/2014 | Andreiko | A61C 7/002 |
| | | | | 433/29 |
| 2016/0008116 | A1* | 1/2016 | Glinec | A61C 9/0053 |
| | | | | 433/29 |

FOREIGN PATENT DOCUMENTS

| KR | 10-1439283 B1 | 9/2014 |
|---|---|---|
| KR | 10-1473192 B1 | 12/2014 |
| KR | 10-1613159 B1 | 4/2016 |
| WO | WO 2010/091868 A1 | 8/2010 |

OTHER PUBLICATIONS

Gwen R. J. Swennen et al., "A Cone-Beam Computed Tomography Triple Scan Procedure to Obtain a Three-Dimensional Augmented Virtual Skull Model Appropriate for Orthognathic Surgery Planning", The Journal of Craniofacial Surgery, Mar. 2009, pp. 297-307, vol. 20, No. 2.

Gwen R. J. Swennen et al., "Three-Dimensional Treatment Planning of Orthognathic Surgery in the Era of Virtual Imaging", J. Oral Maxillofac Surg, 2009, pp. 2080-2092, vol. 67.

* cited by examiner

METHOD, APPARATUS AND PROGRAM FOR SELECTIVE REGISTRATION THREE-DIMENSIONAL TOOTH IMAGE DATA TO OPTICAL SCANNING TOOTH MODEL

TECHNICAL FIELD

The present disclosure relates to a method for registering a tooth image model obtained from a three-dimensional tooth imaging apparatus with an accurate tooth image, and more particularly, to an image model registering method for performing registration of a tooth image model, a bite model obtained by an optical scanner and a tooth scanning model, and an apparatus and a computer program therefore.

DESCRIPTION OF THE RELATED ART

In surgeries near teeth such as implant, double jaw surgery and calibration, it is necessary to obtain accurate medical images for detailed surgical planning. To obtain patients' medical images, Computed Tomography (CT) has been used, and recently, many dental facilities primarily use Cone-Beam Computed Tomography (CBCT) to diagnose patients' teeth and obtain teeth images. General methods for obtaining teeth images using CT and CBCT are relatively easy to extract skin and facial bones. However, images of teeth (surface, structure, etc.) themselves are not obtained accurately, and when there is a metal material such as a calibration device and dental prosthesis on or around teeth, CT images may contain noise such as ghosting or artifact, resulting in data loss at a part containing noise. Its consequential problem is that the teeth shape is inaccurate and distorted teeth images are obtained.

To overcome this, earlier technology uses a method which makes a palatal fiducial marker, fixes the marker in a patient's mouth, takes scan images through CT, makes a patient's tooth bite, fixes another marker to the bite, optically scans, and performs coordinate system registering through the markers present in each scan data.

Another earlier technology uses a method which 1) takes CBCT for a patient biting a bite having a marker attached thereto, 2) independently takes CBCT for the bite with high output, 3) optically scans the bite, 4) optically scans the patient's tooth, 1)-2) performs registration based on the marker, 2)-3) performs registration based on the model surface, 3)-4) performs registration based on the model surface, and as a result, registers the tooth model to the patient's CBCT image.

Still another earlier technology uses CBCT multiple times.

The foregoing earlier technologies require patients' exposure to CBCT scans multiple times, increasing the patients' amount of radiation exposure, and fail to scan accurate teeth structures and have limitations in obtaining accurate teeth images.

SUMMARY

An object according to an aspect of the present disclosure is to provide a registration method, apparatus and computer program that can obtain a more accurate tooth image by registering a directly scanned tooth structure to patient's minimum exposure to CBCT and reduced amount of radiation exposure.

A method for registering a tooth image to a tooth structure according to an embodiment may include a first registering step for registering a tooth image model obtained from a medical image taken when an object bites a bite including a marker to a bite scanning model obtained by scanning the bite, a second registering step for registering the bite scanning model to a tooth scanning model obtained by scanning a tooth structure of the object, and a third registering step for registering the tooth image model to the tooth scanning model based on the results of the first registering step and the results of the second registering step.

The bite scanning model or the tooth scanning model may be obtained from an image generated using an optical scanner.

The first registering step may further include setting the marker included in the tooth image model as a first region of interest, disposing the bite scanning model and the tooth image model within a predetermined distance gap based on the marker included in the bite scanning model and the first region of interest, setting the marker included in the bite scanning model as a second region of interest, and moving the tooth image model or the bite scanning model so that the distance between at least one reference point of the first region of interest and at least one reference point of the second region of interest corresponding to the at least one reference point of the first region of interest is minimum.

The setting of the marker included in the tooth image model as the first region of interest may include displaying at least one of the marker included in the tooth image model, a tooth part and a structure installed at the tooth based on a preset Hounsfield Unit (HU) value, determining a position of the marker by the user input for the displayed marker, and setting a region within a predetermined range based on a radius value of the marker as the first region of interest based on the determined position of the marker.

The setting of the marker included in the bite scanning model as the second region of interest may further include setting a start triangle at a start point of the user input for the bite scanning model within a predetermined region selected through the user input for the bite scanning model, searching for a neighboring triangle sharing at least one of three vertices of the start triangle based on the start triangle, iteratively searching for another neighboring triangle sharing at least one of three vertices of the neighboring triangle based on the neighboring triangle, and setting a region covered with the start triangle and the multiple found neighboring triangles in the bite scanning model as the second region of interest.

The searching for the neighboring triangle may include, when at least one of three vertices of any one found neighboring triangle is outside of the region selected through the user input, stopping searching for another neighboring triangle sharing one of three vertices of the neighboring triangle.

The second registering step may include disposing the bite scanning model and the tooth scanning model within a predetermined distance gap, setting the tooth part included in the bite scanning model as a third region of interest, setting the tooth part included in the tooth scanning model as a fourth region of interest, and moving the bite scanning model or the tooth scanning model so that the distance between at least one reference point of the third region of interest and at least one reference point of the fourth region of interest respectively corresponding to the at least one reference point of the third region of interest is minimum.

The setting of the tooth part included in the bite scanning model as the third region of interest or the setting of the tooth part included in the tooth scanning model as the fourth region of interest may include setting a start triangle at a start point of the user input in each predetermined region selected through the user input for the bite scanning model or the tooth scanning model, searching for a neighboring triangle sharing at least one of three vertices of the start triangle based on the start triangle, iteratively searching for another neighboring triangle sharing at least one of three vertices of the neighboring triangle based on the neighboring triangle, and setting a region covered with the start triangle and the multiple found neighboring triangles in the bite scanning model as the third region of interest, and a region covered with the start triangle and the multiple found neighboring triangles in the tooth scanning model as the fourth region of interest.

The searching for the neighboring triangle may include, when at least one of three vertices of any one found neighboring triangle is outside of the region selected through the user input, stopping searching for another neighboring triangle sharing one of three vertices of the neighboring triangle.

The third registering step may include registering the coordinates of the tooth image model to the tooth scanning model using a coordinates result value of the first registering step and a coordinates result value of the second registering step.

The tooth image model may be generated based on the tooth image taken using at least one of Computed Tomography (CT), Cone-Beam Computed Tomography (CBCT), Magnetic Resonance Imaging (MRI), and X-ray.

An apparatus for registering a tooth image to a tooth structure according to an embodiment may include a data acquisition unit configured to obtain a tooth image model generated from a tooth image taken when an object bites a bite including a marker, a bite scanning model generated by scanning the bite, and a tooth scanning model generated by scanning a tooth structure of the object, a display unit, a first region of interest model setting unit configured to set the marker included in the tooth image model as a first region of interest, a second region of interest setting unit configured to set the marker included in the bite scanning model as a second region of interest, set the tooth part included in the bite scanning model as a third region of interest, and set the tooth part included in the tooth scanning model as a fourth region of interest, a pre-registering unit configured to dispose at least one of the tooth image model, the bite scanning model and the tooth scanning model within a predetermined distance gap from one of the remaining models, and a main registering unit configured to move at least one of the tooth image model, the bite image model and the tooth scanning model so that for two regions of interest of the set first, second, third and fourth regions of interest, the distance between at least one reference point of the two regions of interest is minimum respectively.

A computer program stored in a recording medium according to an embodiment may perform a process in combination with hardware, the process including a first registering step for registering a tooth image model obtained from a medical image taken when an object bites a bite including a marker to a bite scanning model obtained by scanning the bite, a second registering step for registering the bite scanning model to a tooth scanning model obtained by scanning a tooth structure of the object, and a third registering step for registering the tooth image model to the tooth scanning model based on the results of the first registering step and the results of the second registering step.

As a result according to an aspect of the present disclosure, an accurate shape of a tooth part difficult to obtain from a medical imaging apparatus can be obtained through optical scanning, and accuracy in registration of coordinate system to a tooth image can be further improved. Accordingly, a model including an accurate tooth shape can be easily obtained, and it can be usefully used in virtual surgical planning of double jaw surgery, calibration and implant by registration to a skin and bone model obtained from the tooth image.

DETAILED DESCRIPTION

Figure 1:
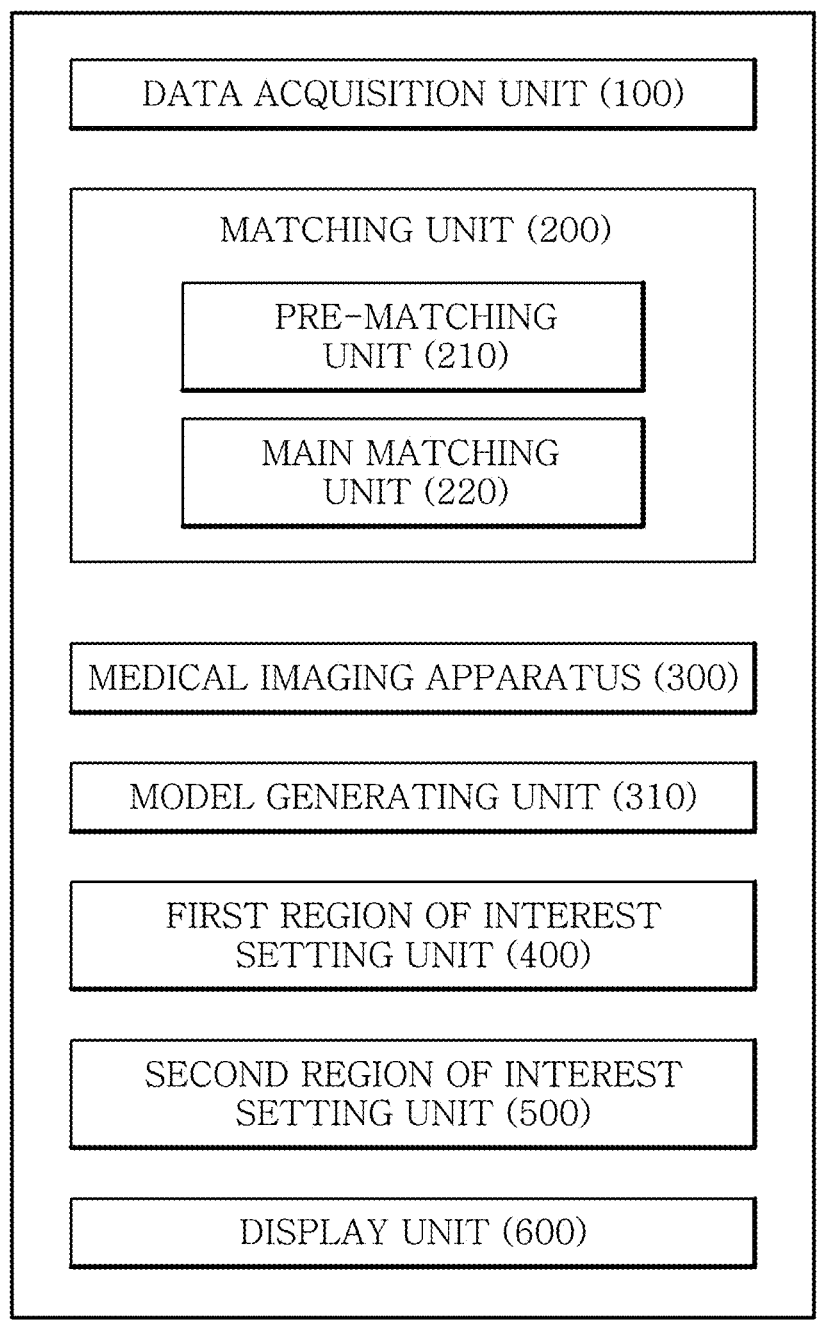
FIG. 1 is a block diagram of an apparatus for registering 3-dimensional (3D) tooth image data to an optical scanning tooth model according to an embodiment of the present disclosure.

Embodiments will be described with reference to the accompanying drawings. However, the disclosed principles may be implemented in many different forms and should not be understood as being limited to the disclosed embodiments. In the detailed description, certain detailed description of well-known features and technology may be omitted herein to avoid rendering the features of the embodiments unnecessarily vague.

In the drawings, reference numerals in the drawings indicate components. For clarity, the shape, size, area, etc. in the drawings may be exaggerated.

The term "image" as used herein refers to multi-dimensional data composed of discrete image elements (for example, pixels in a 2-dimensional (2D) image and voxels in a 3-dimensional (3D) image). For example, the image may include medical images of an object obtained by X-ray, CT, MRI, an ultrasonic wave, and other medical imaging system.

The "object" may include a human or an animal or parts of a human or an animal. In an embodiment, the object may be a patient who desires a tooth related surgery.

A method according to an embodiment of the present disclosure may be implemented in the form of a computer program for performing a series of processes, and the computer program may be a computer-readable recording medium. Furthermore, the computer program may be executed in combination with hardware.

Hereinafter, a description for practicing the present disclosure will be provided in detail with reference to the accompanying drawings.

FIG. 1 is a block diagram of an apparatus 1000 for registering 3D radiography tooth image data to an optical scanning tooth model according to an embodiment of the present disclosure. The apparatus 1000 may include a data acquisition unit 100 and a registering unit 200, and the registering unit 200 may include a pre-registering unit 210 and a main registering unit 220.

Furthermore, in an embodiment, the apparatus 1000 may further include at least one of a first region of interest setting unit 400, a second region of interest setting unit 500, and a display unit 600.

Figure 2A:
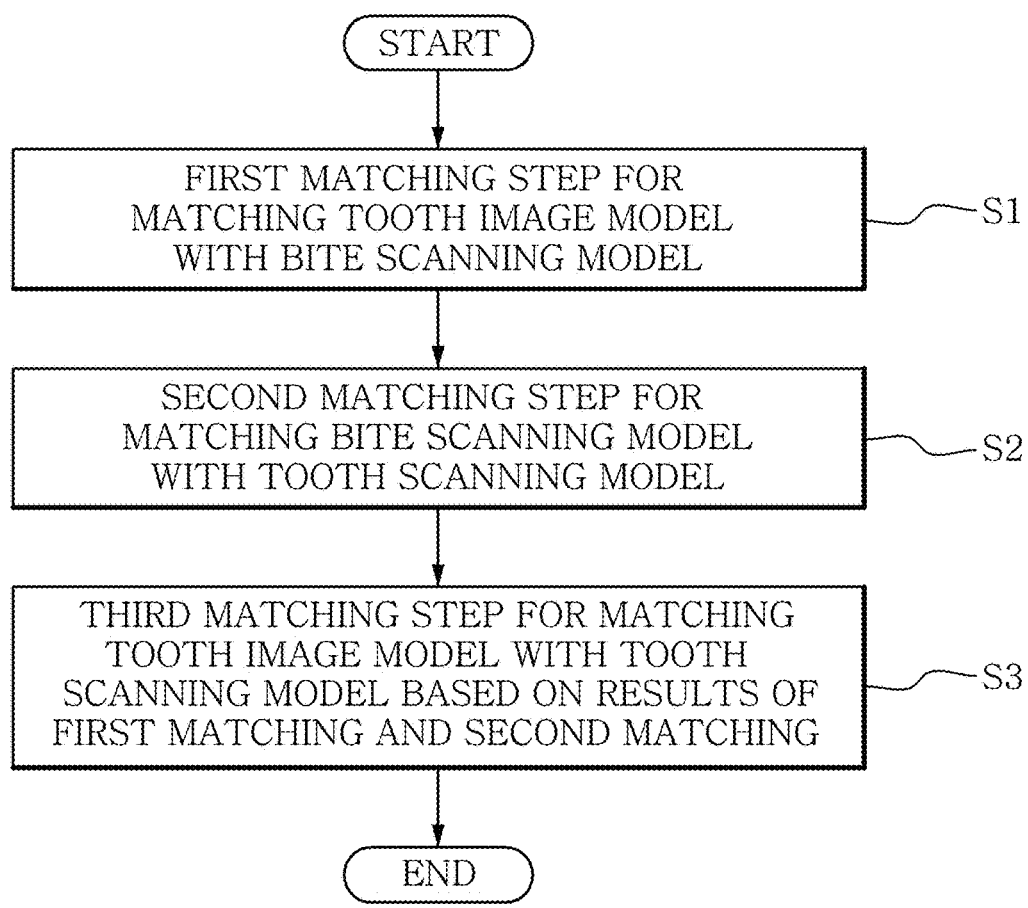
FIG. 2A is a flowchart of a method for registering 3D tooth image data to an optical scanning tooth model according to an embodiment of the present disclosure.

FIG. 2A is a flowchart of a method for registering 3D radiography tooth image data with an optical scanning tooth model, and the method for registering 3D radiography tooth image data to an optical scanning tooth model may be implemented by the components of the apparatus 1000.

The method for registering a tooth image to a tooth structure includes a first registering step (S1) of registering a tooth image model including a face of an object to a bite scanning model obtained by scanning a bite, wherein the tooth image model is obtained from a medical image taken when the object bites the bite including a marker, a second registering step (S2) of registering the bite scanning model to a tooth scanning model obtained by scanning a tooth structure of the object, and a third registering step (S3) of registering the tooth image model to the tooth scanning model based on the results of the first registering step and the results of the second registering step, and as a result, an embodiment of the present disclosure may provide an image obtained by registering the tooth image including the face of the object to the accurate tooth structure of the object.

Referring to FIGS. 1 and 2A to 2D, the data acquisition unit 100 may acquire data generated through a medical imaging apparatus, or a tooth image model 10 including a patient's face generated from a medical image taken when the object bites a bite including a marker, a bite scanning model 20 generated by scanning the bite, and a tooth scanning model 30 generated by scanning the tooth structure of the object. Furthermore, raw data observed from the medical imaging apparatus or measured data may be acquired.

Figure 2B:
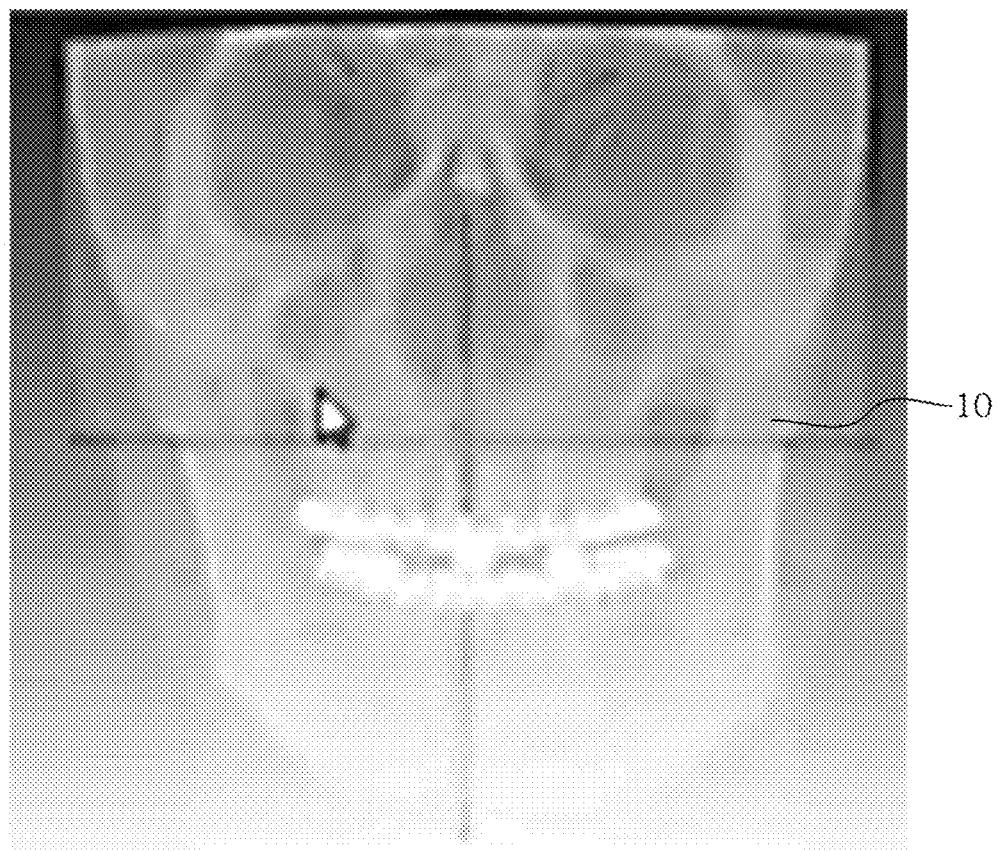
FIG. 2B is a diagram of a tooth image model.
Figure 2C:
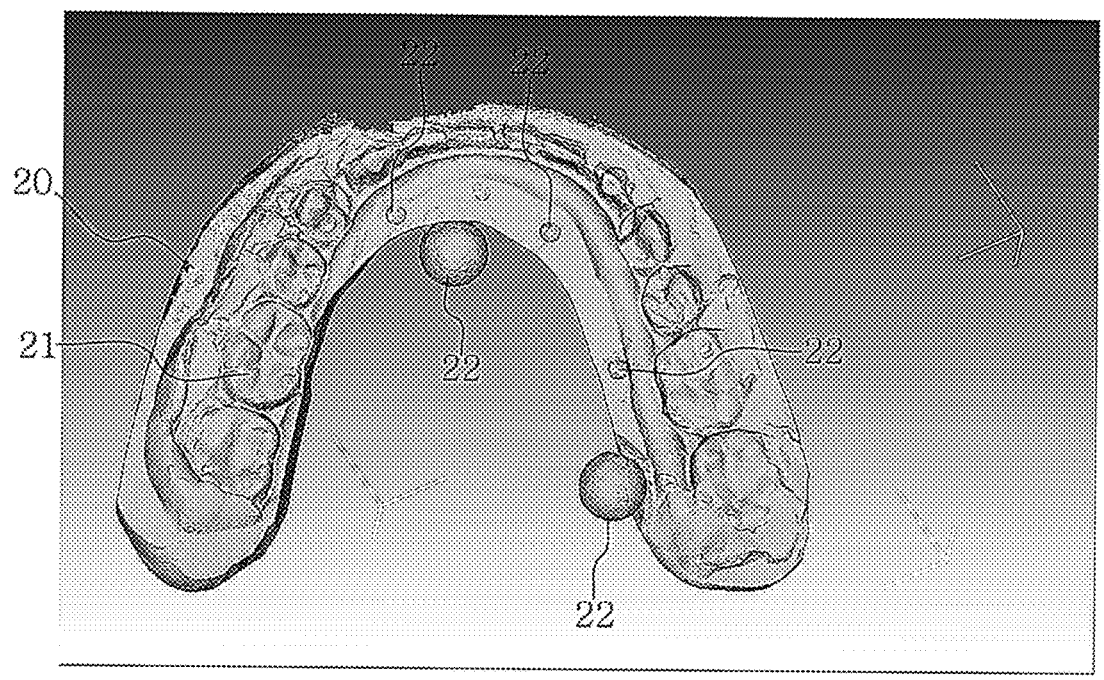
FIG. 2C is a diagram of a bite scanning model.
Figure 2D:
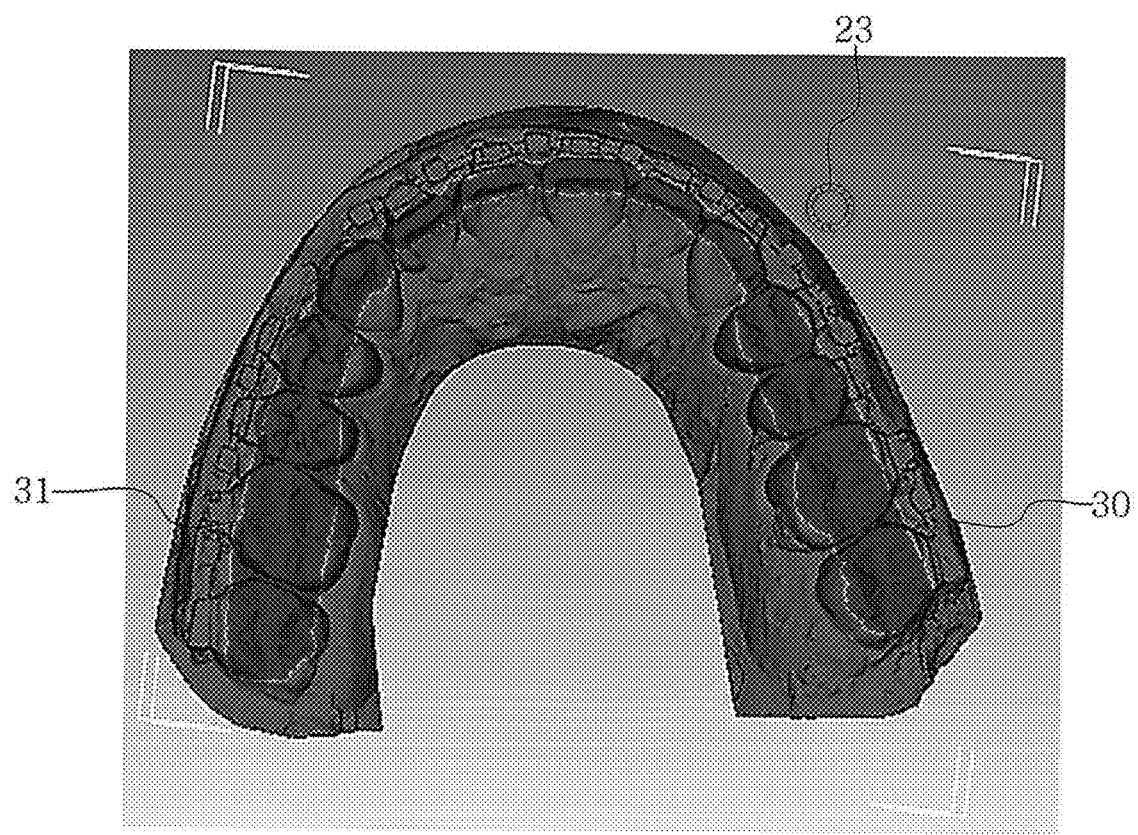
FIG. 2D is a diagram of a tooth scanning model.
Figure 3A:
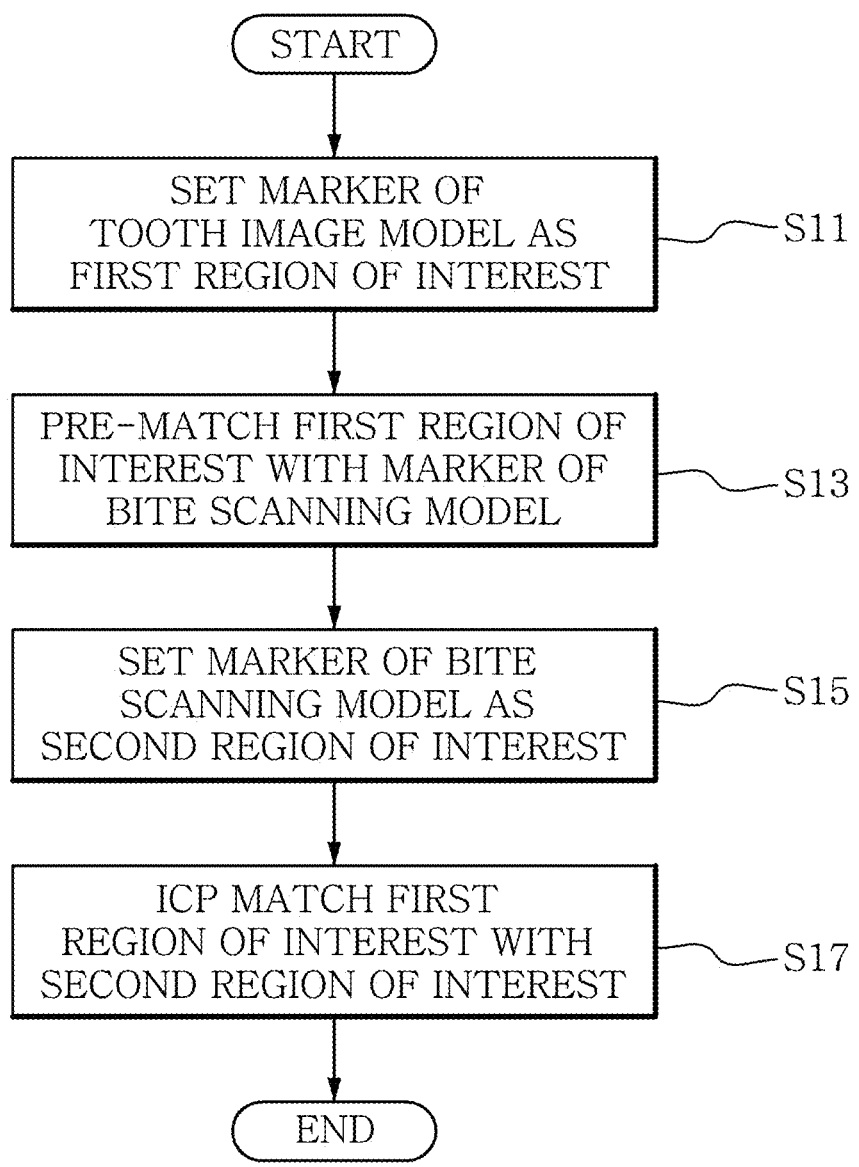
FIG. 3A is a flowchart of a first registering step according to an embodiment.
Figure 3B:
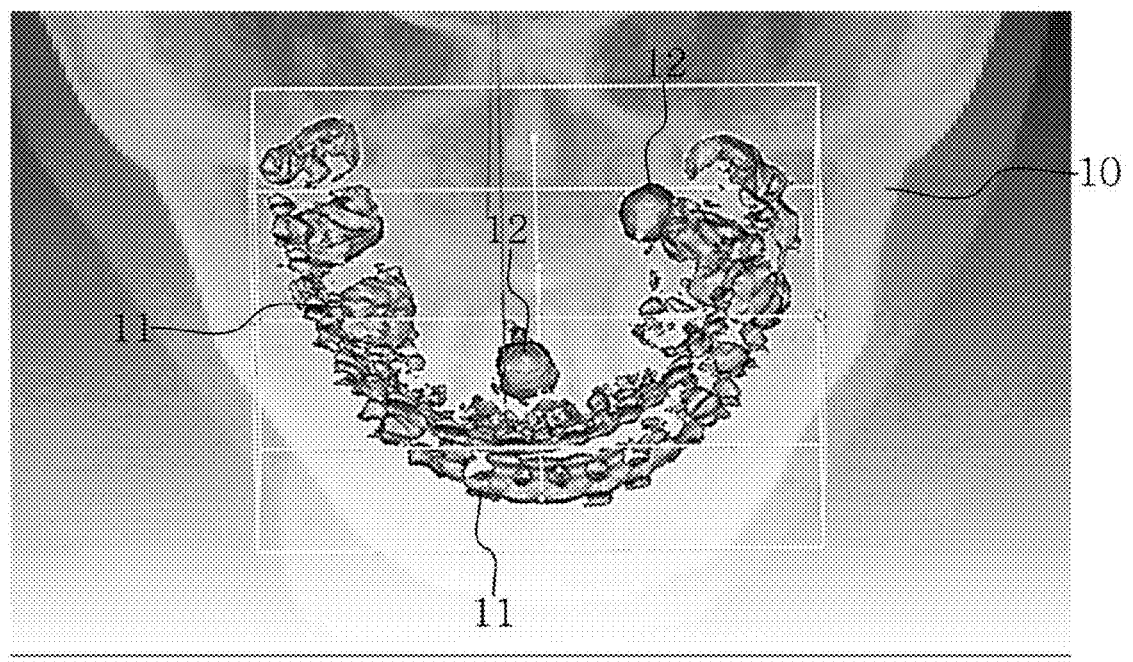
FIG. 3B is a diagram showing a marker included in a tooth image model, a tooth part, and a structure installed at the tooth, based on a preset HU value.

In an embodiment, the data acquisition unit 100 may obtain the tooth image model 10 generated from the medical image taken when the patient bites the bite including the marker. As shown in FIG. 2B, the tooth image model 10 may be, for example, a model for a face image including tooth generated from the medical imaging apparatus, such as an image model including face and tooth parts generated by taking CBCT for the patient's face. Alternatively, as shown in FIG. 3B, the tooth image model may be, for example, a model for a tooth image generated by limiting an image including face and tooth parts to the tooth, wherein the image including face and tooth is generated by taking CBCT for the facial part.

In another embodiment, the apparatus 1000 includes the data acquisition unit 100 as well as a medical imaging apparatus 300 and a model generating unit 310. In the embodiment, when the medical imaging apparatus 300 is, for example, CBCT, the data acquisition unit 100 may acquire data by imaging the object from the CBCT. Specifically, the data acquisition unit 100 may receive raw data from the CBCT, and obtain a 2D CT image or a 3D CT image generated by the model generating unit 310 using the raw data. Specifically, as shown in FIG. 3B, using Digital Imaging and Communications in Medicine (DICOM) data acquired by taking CBCT, the model generating unit 310 may generate the 3D tooth image model 10 through a segmentation process into a skin region, a skull region except tooth, and a marker region.

The display unit 600 may provide the obtained tooth image model in an embodiment. In another embodiment, the display unit 600 may provide a CT image model generated by the model generating unit 310. Specifically, the display unit 600 may provide a tooth image model which is a target image model.

The data acquisition unit 100 may obtain the tooth shape of the object generated because the object bites when taking the tooth image and a bite scanning model 20 generated by scanning the bite including the marker. An embodiment of the present disclosure may include at least one marker in the bite structure without directly attaching the marker to the tooth part of the object, for example, the object's gingiva or inner part of the lips. If the marker is directly attached to the tooth part of the object, the position of the marker may be moved from the original position due to the friction during taking a medical image. Accordingly, when the marker is included in the bite structure, the position of the marker can be calculated more accurately at the time of taking an image.

In still another embodiments, the apparatus 1000 may include a scanning unit. The scanning unit may scan the bite and the tooth of the object to generate scan images, and generate each scanning model from the scan images. The scanning unit may include a contact or non-contact type scanner. However, in a preferred embodiment, using a non-contact type scanner may be advantageous because when a contact-type scanner is used to scan the bite, scanning is performed with a probe in direct contact with the object surface, causing deformation and damage of the object.

In the embodiment, an optical scanner may be used to generate the bite scanning model. The optical scanner projects light of stripe shape from large to small width multiple times, calculates images by triangulation to acquire data in a sequential order, and puts together the images of data acquired in many directions to acquire final data of the object. Accordingly, advantages are that a scan rate is fast, clear images can be obtained, and an amount of radiography exposure can be reduced compared to radiography imaging.

The apparatus 1000 may include the first region of interest setting unit 400 to set the marker included in the tooth image model as a first region of interest 13. For example, in the case of the tooth image model 10 generated based on a medical image such as CBCT, the tooth structure included in the tooth image model 10 is not clear, whereas the marker 12 may be seen relatively clearly. Accordingly, the marker may be used as a more accurate reference when registering the tooth image model to the tooth scanning model.

Referring to FIGS. 3B and 4, first, the first region of interest setting unit 400 may set the marker included in the tooth image model as a first region of interest based on a preset Hounsfield Unit (HU) value (S11). Each material differs in the extent of radiography absorption, and a HU value (or CT numbers) represents the extent of absorption. In an embodiment, the data acquisition unit 100 may obtain results generated by taking CBCT when the object bites the bite including the marker. Based on the results, the first region of interest setting unit 400 may set the first region of interest 13 of the tooth image model. In another embodiment, as shown in FIG. 3B, based on DICOM data obtained by taking CBCT and the preset HU value of the marker, the model generating unit 310 may generate the marker 12, the tooth part and the structure 11 installed at the tooth through volume rendering and display them through the display unit 600. In this instance, when the user inputs the position of the marker, for example, when the user clicks the displayed marker 12, the first region of interest setting unit 400 may set, as the region of interest 13, a region within a predetermined range, for example, twice the marker radius, from the position of the marker clicked by the user, and may set all the set regions of interest as the first region of interest 13 by iteratively performing this process on each of all the markers 12 included in the tooth image model. In another embodiment, the first region of interest setting unit 300 may separately extract and model only a region set as the first region of interest 13. FIG. 2F is a diagram showing extraction and modeling of only the first region of interest 13 set for the marker 12 included in the tooth image scanning model.

In still another embodiment, the user's selection may be a touch. In this case, the display unit 600 may include a touch sensor.

Figure 3C:
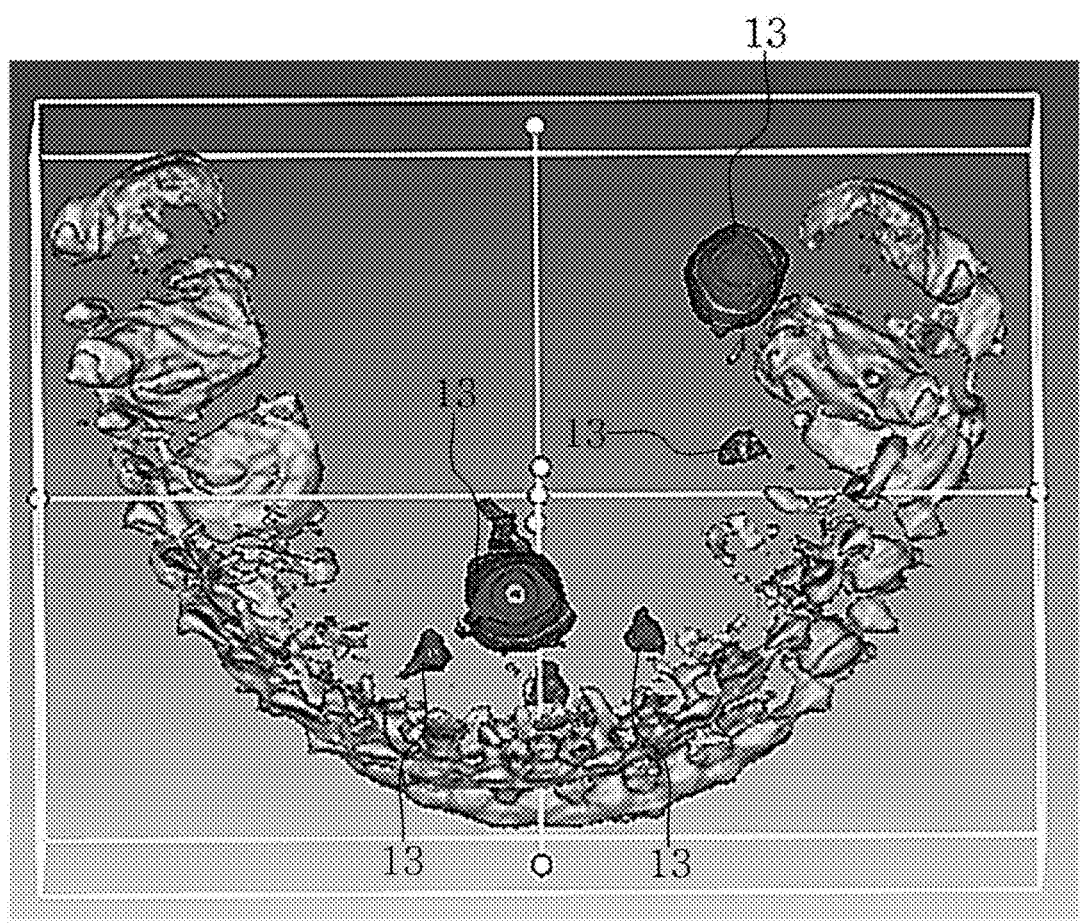
FIG. 3C is a diagram showing a first region of interest set on a tooth image model.
Figure 3D:
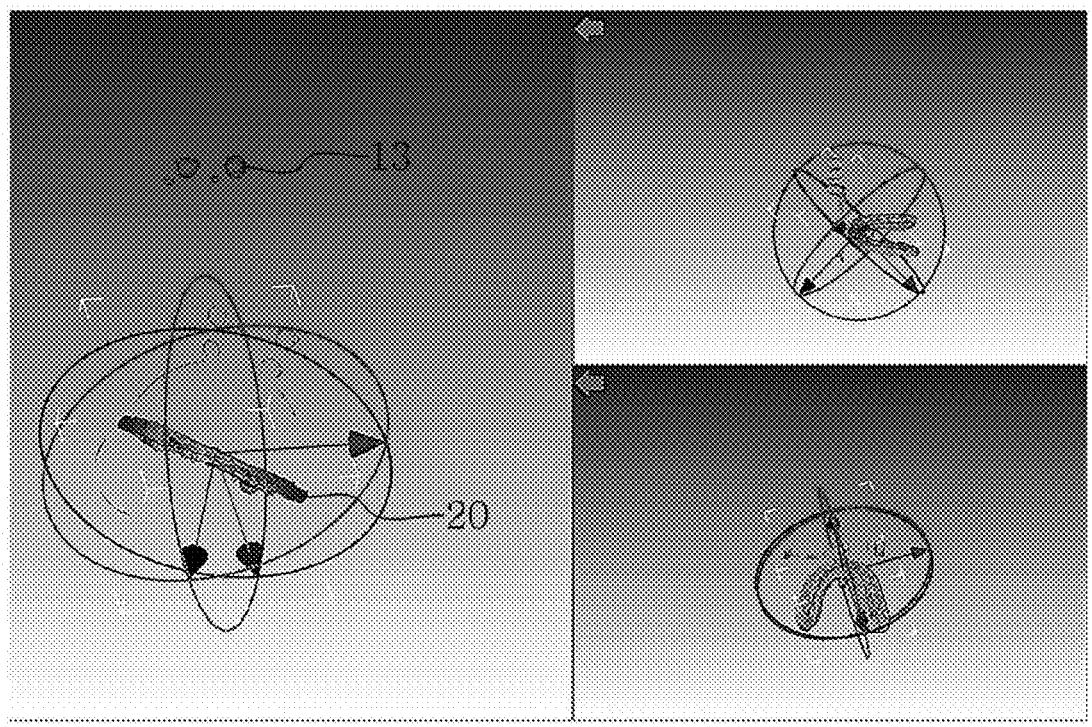
FIGS. 3D and 3E are diagrams showing the disposing of a bite scanning model and a tooth image model within a predetermined distance gap.
Figure 3E:
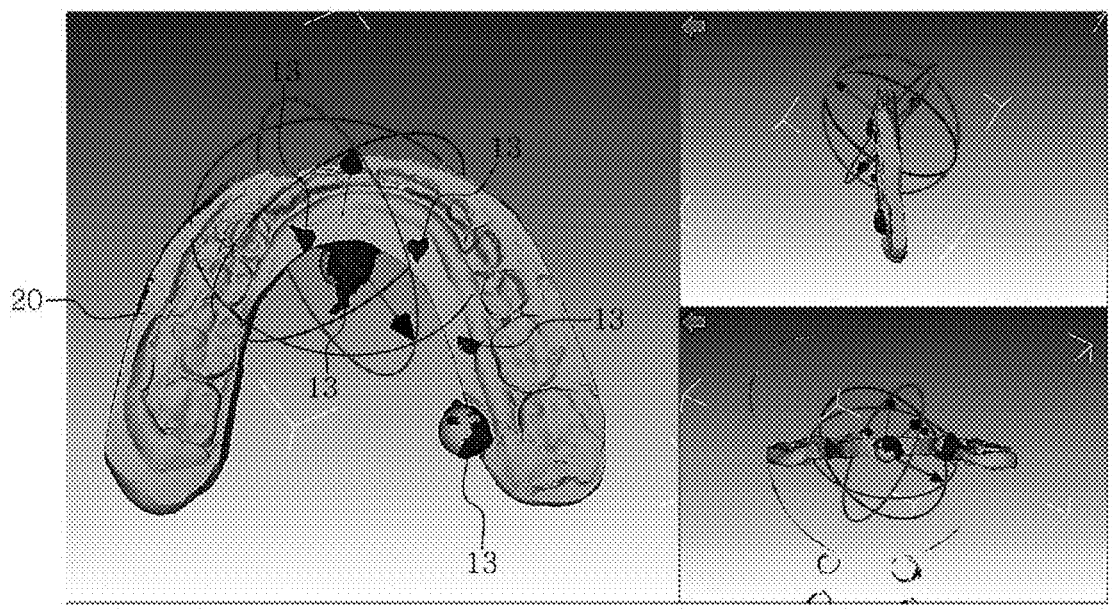

The pre-registering unit 210 may dispose the bite scanning model and the tooth image model within a predetermined distance gap, based on the first region of interest and the marker included in the bite scanning model (S13). That is, in an embodiment, the step S13 is a preliminary registering step before accurately registering the tooth image model to the bite scanning model. The pre-registering unit 210 may register the tooth scanning model 10 with the bite scanning model 20 within a predetermined distance gap, i.e., roughly register the tooth scanning model 10 with the bite scanning model 20. Referring to FIGS. 3C and 3D, to improve convenience and accuracy and easily understand the current preliminary registering condition, the pre-registering unit 210 may easily dispose the bite scanning model or the tooth image model within a predetermined distance gap by providing multiple duplicated views and making position movement or rotary movement. In another embodiment, the pre-registering unit 210 may pre-register the bite scanning model to a model generated by separately extracting and modeling only the region set as the first region of interest 13. That is, as shown in FIGS. 3D and 3E, the bite scanning model may be disposed within a predetermined distance gap from a model generated by separately extracting and modeling only the region set as the first region of interest 130 (S13).

The second region of interest setting unit 500 may set the marker included in the bite scanning model as a second region of interest, based on a predetermined region selected by the user input (S15). In an embodiment, the user input for region selection may be a mouse drag. In another embodiment, the user input for region selection may be a touch. In this case, the display unit 600 may include a touch sensor.

Figure 4A:
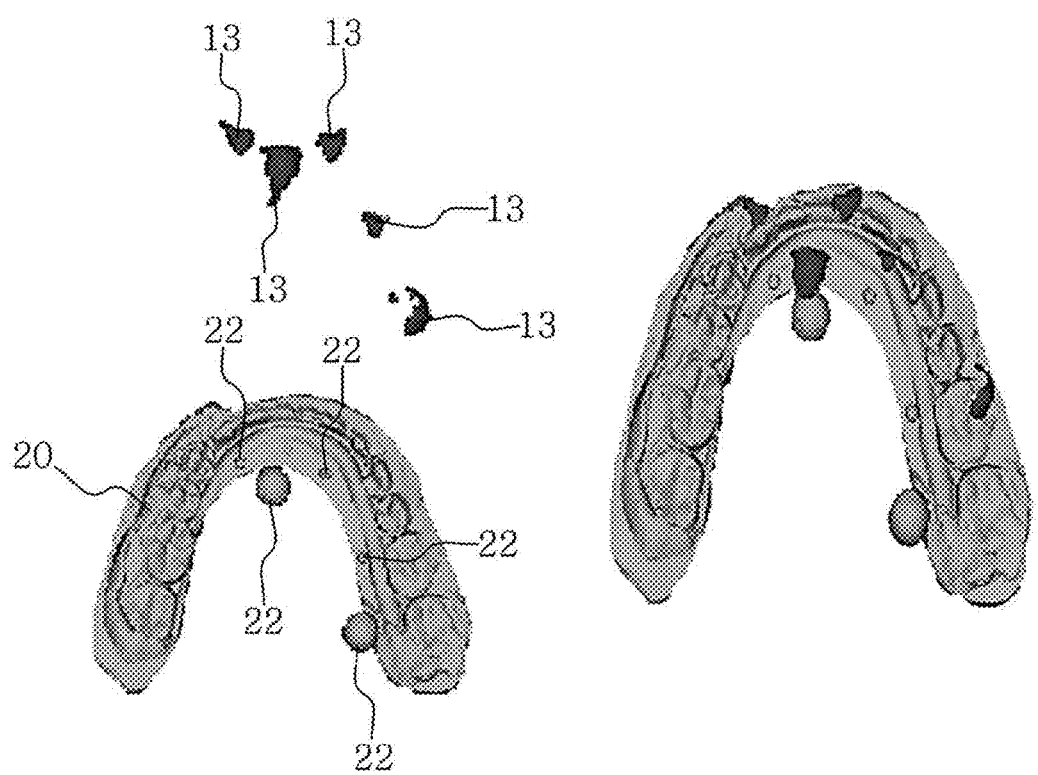
FIG. 4A is a diagram showing the results of registering by executing an ICP algorithm without setting a region of interest according to a conventional method.
Figure 4B:
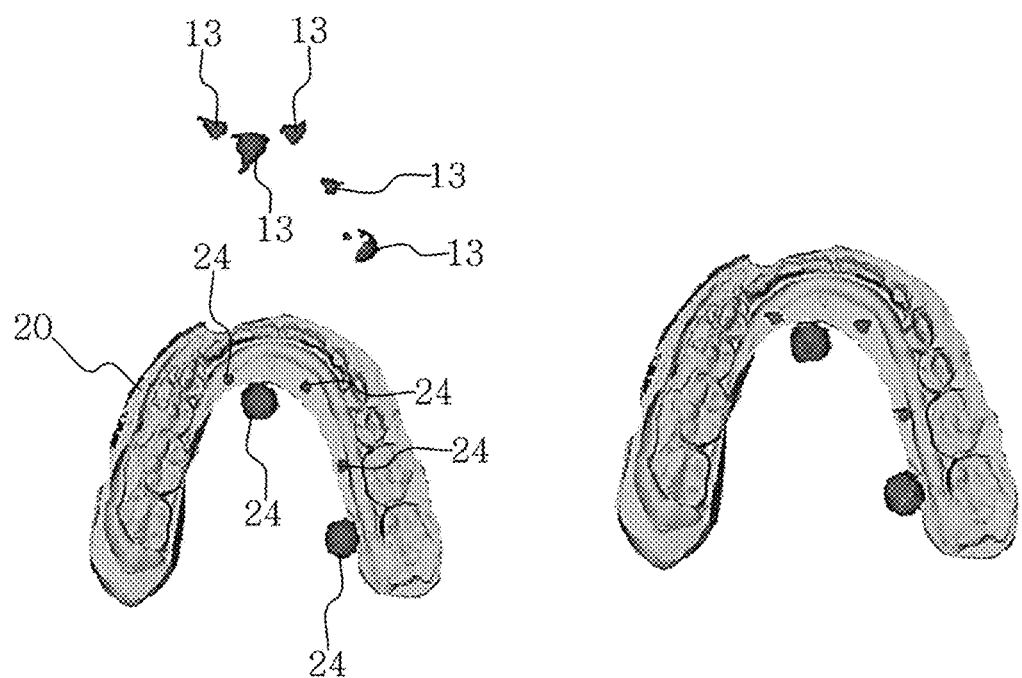
FIG. 4B is a diagram the results of registering by executing an ICP algorithm after setting a region of interest according to an embodiment of the present disclosure.
Figure 4C:
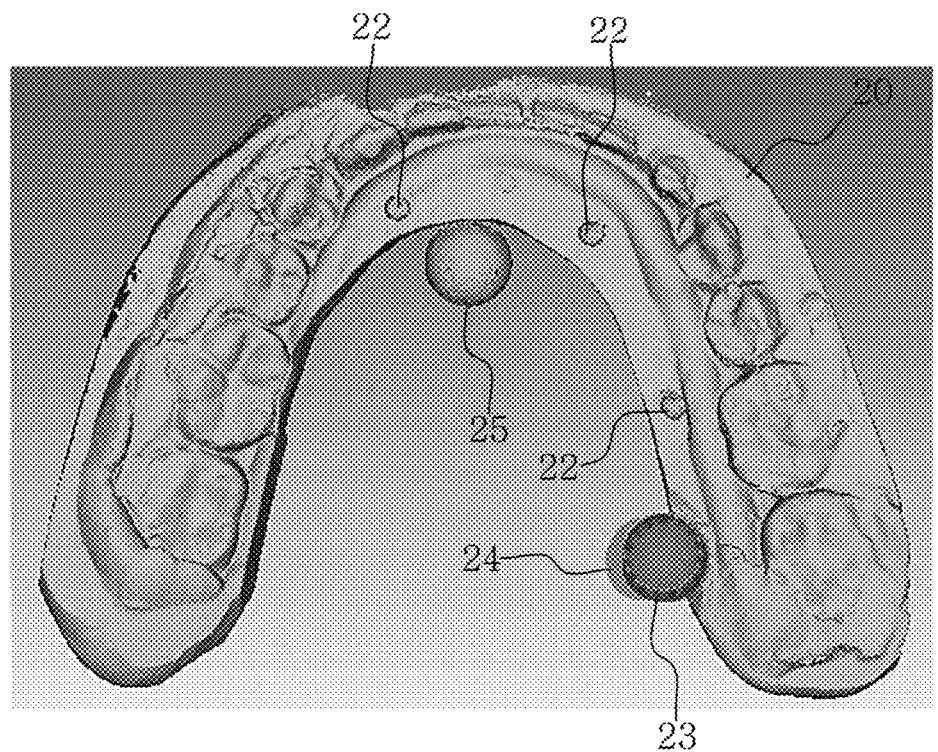
FIG. 4C is a diagram the displaying of a predetermined region selected through a user input on a bite scanning model at the step of setting a second region of interest.

In an embodiment, as shown in FIG. 4C, when the user enters a region of interest setting mode, the second region of interest setting unit 500 may generate a virtual 2D circle 23 having a preset radius at the position of the mouse cursor on the 2D screen. The user may move the virtual 2D circle 23 through the mouse or touch drag. When the 2D circle is moved by the user, the second region of interest setting unit 500 may paint all pixels included in the position, to which the 2D circle moved, in semitransparent color, to display a predetermined region 24 to select through the display unit 600 beforehand.

In an embodiment, when the user drags and takes off the left button of the mouse, setting of the second region of interest in the bite scanning model may begin. First, the second region of interest setting unit 500 may set a start triangle at a start point of the user input in the predetermined region 24 selected through the user input (3D Mesh Picking). Based on the start triangle, the second region of interest setting unit 500 searches for a neighboring triangle sharing at least one of three vertices of the start triangle, and based on the neighboring triangle, iteratively searches for another neighboring triangle sharing at least one of three vertices of the neighboring triangle again, and thus, may expand an region covered with the start triangle and the multiple found neighboring triangles.

Figure 4D:
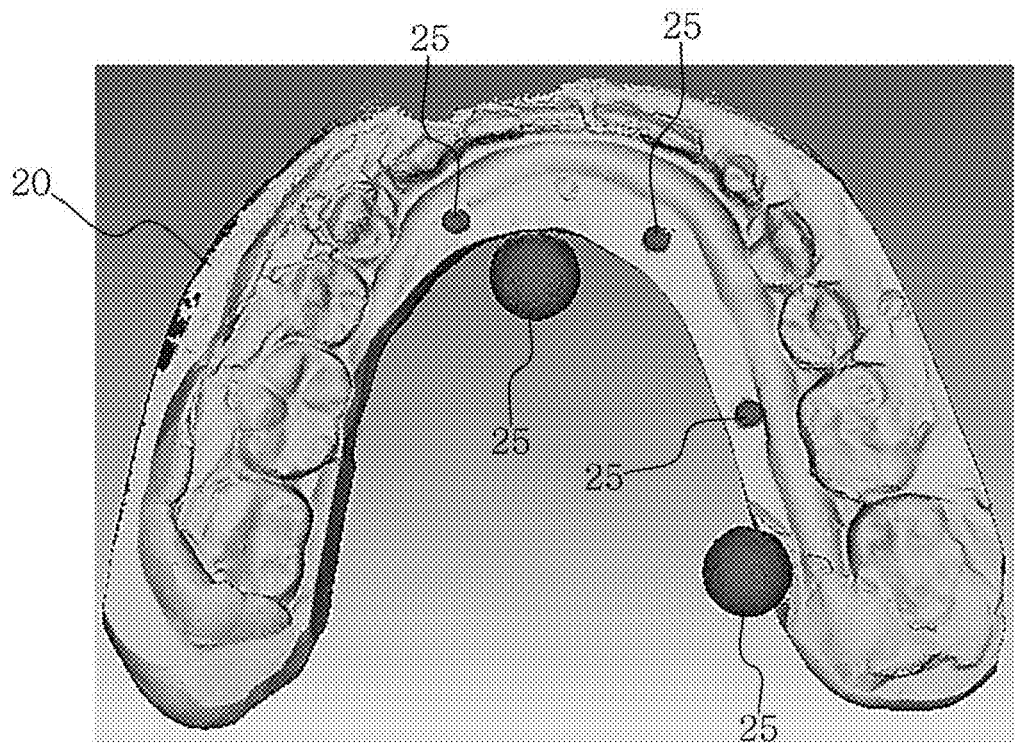
FIG. 4D is a diagram showing a second region of interest set on a bite scanning model.
Figure 4E:
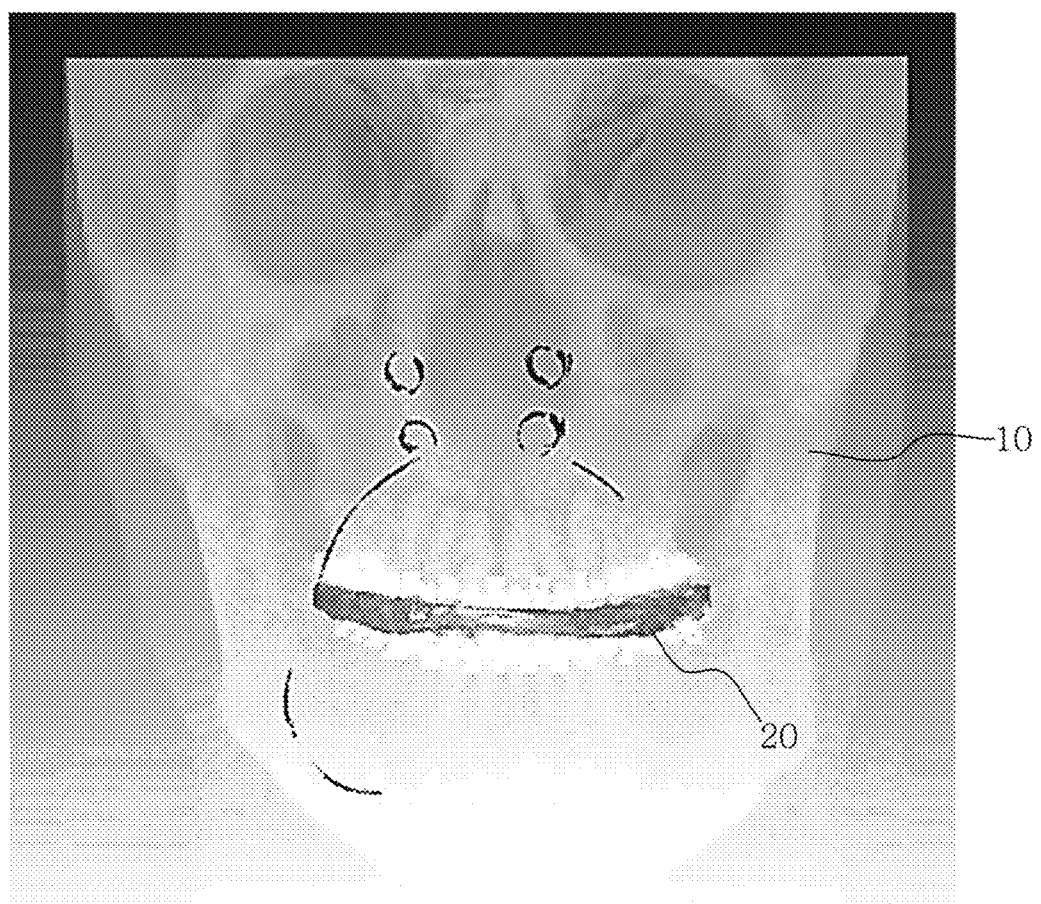
FIG. 4E is a diagram showing the registering of a bite scanning model to a tooth image model.

Additionally, at the expanding step, the second region of interest setting unit 500 projects each vertex of the expanded neighboring triangle plane onto the 2D screen along the projection matrix of graphics pipeline and examines whether the projected point corresponds to the pixel of the predetermined region 24 selected by the user. If all of the three vertices of the neighboring triangle plane correspond to colored pixels while searching for the neighboring triangle plane, the second region of interest setting unit 500 sets the found neighboring triangle to be included in the second region of interest, and successively continues to search for another neighboring triangle sharing the vertices of the included neighboring triangle plane. If any one of the vertices of the neighboring triangle plane is projected onto an uncolored pixel while searching the neighboring triangle plane, the second region of interest setting unit 500 does not search for another neighboring triangle any longer based on the corresponding neighboring triangle, and as a result, the second region of interest is not expanded and is set based on the position of the latest found neighboring triangle. When this process repeats, a second region of interest 25 of the bite scanning model, projected onto the predetermined region 24 selected by the user may be set as shown in FIG. 4D (S15).

Further, after pre-registering, the main registering unit 220 may register the tooth image model with the bite scanning model using the second region of interest 25 set by the user input (S17).

When the setting of the region of interest selected by the user input is used, a registering failure situation can be reduced. For example, as shown in FIG. 4B, when only the marker 22 of the bite scanning model 20 is set as the region of interest 25, the main registering unit 220 may calculate a position at which an average of distances from reference points or all vertices that make up the region of interest 25 of the bite scanning model to the marker of the tooth image model is minimum. As a result, the marker 12 of the tooth image model may be disposed at the position of the marker 22 of the bite scanning model.

Here, the failure situation of registration refers to 1) a situation of calculating a position at which an average of distances from all vertices that make up the bite scanning model to the tooth image model is minimum when registering is performed using the conventional ICP (Iterative Closest Point) algorithm, and 2) a situation of calculating a position at which an average of distances from reference points or all vertices that make up the bite scanning model to an extracted and modeled marker is minimum when the marker of the tooth image model is set as the first region of interest and extracted and modeled, and registering is performed using the conventional ICP algorithm.

More specifically, 1) registration is performed to have a distance closet to points on the first region of interest of the tooth image model surface from reference points or vertices of all regions of the bite scanning model 20, which deviates from the intent to use the marker as reference point coordinates for registering, and 2) ICP registration is performed at vertices of all regions of the bite scanning model, so there is a problem that inaccurate registering results may be derived. If a process for finding a closet point using the ICP algorithm is incorrectly calculated, the algorithm execution time increases and the registering accuracy reduces. For example, as shown in FIG. 4A, the position is calculated at which an average of distances from reference points or all vertices of the bite scanning model 20 is minimum when registering the marker 22 of the bite scanning model 20 to the marker 13 of the tooth image model using ICP algorithm without setting the region of interest. As a result, the marker 12 of the tooth image model may not be disposed at the position of the marker 22 of the bite scanning model 20.

The main registering unit 220 may move the bite scanning model or the tooth image model so that an average of distances between at least one reference point of the first region of interest and at least one reference point of the second region of interest respectively corresponding to at least one reference point of the first region of interest is minimum (S17). In an embodiment, the main registering unit 220 may determine at least one reference point included in the first region of interest 13 set at the step S11, through ICP algorithm. The main registering unit 220 may determine at least one reference point corresponding to at least one reference point of the first region of interest, included in the second region of interest 25 set at the step S15. When the tooth image model or the bite scanning model is moved so that an average of distances between at least one reference point included in the first region of interest and the second region of interest is minimum (S17), as a result, the tooth image model and the bite scanning model may be registeration. That is, as the first region of interest 13 and the second region of interest 25 register, the tooth image model 10 and the bite scanning model 20 may be registration. The reference point may be differently set depending to the situation. For example, in the case of the second registering step (S2) as described below, the reference point may be a point that efficiently represents the silhouette or shape of the bite scanning model, such as a corner included in the silhouette or shape of the bite scanning model. In another embodiment, the main registering unit 220 may move the bite scanning model 20 so that an average of distances between all vertices that make up the second region of interest 25 and the first region of interest 13 is minimum (S17). Referring to FIG. 4B, a minimum average of distances between the first region of interest 13 and the second region of interest 25 may produce a result in which the position of the marker 12 of the tooth image model almost be registered the position of the marker 22 of the bite scanning model. As a result, the tooth image model 10 and the bite scanning model 20 may be registration. In another embodiment, the main registering unit 220 may move the tooth image model 10 so that an average of distances between all vertices that make up the first region of interest 13 and the second region of interest 25 is minimum (S17).

After registering the first region of interest to the second region of interest using ICP algorithm, finally, the registering unit 200 may register the entire tooth image model to the entire bite scanning model based on the registering results between the regions of interest. As shown in FIG. 3E, as a result of the first registering step, the tooth image model 10 may be registered the bite scanning model 20.

Figure 5A:
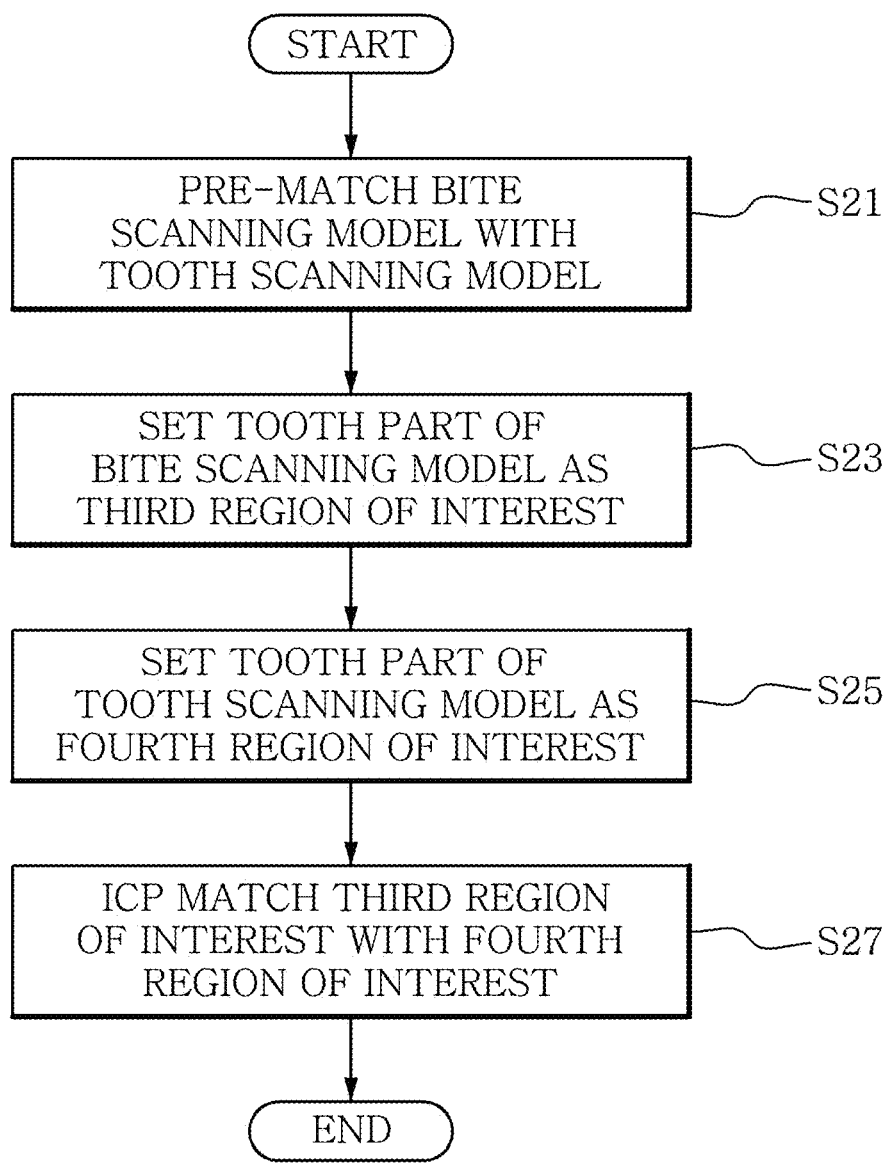
FIG. 5A is a flowchart of a second registering step according to an embodiment of the present disclosure.

The apparatus 1000 may register the bite scanning model to the tooth scanning model through the steps shown in the flowchart of FIG. 5A (S3). At the step S3, to generate a model accurately reflecting the tooth structure of the object, the tooth scanning model 30 may be generated by directly scanning the tooth of the object. The tooth scanning model 30 may be generated using a contact or non-contact type scanner. However, in a preferred embodiment, to reduce the risk of tooth damage, the tooth scanning model may be generated using a non-contact type scanner. In an embodiment, the tooth scanning model may be generated using an optical scanner.

Figure 5B:
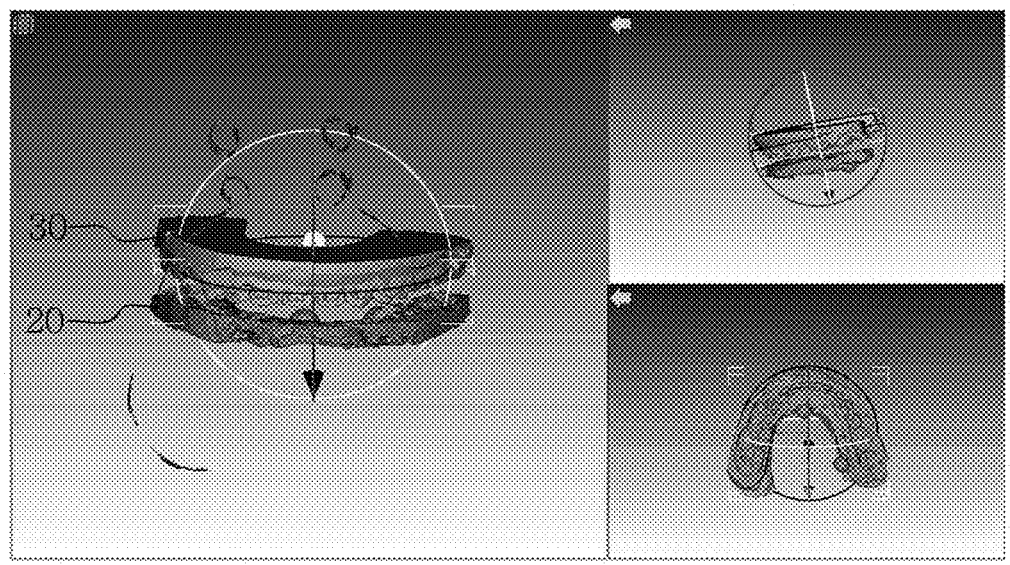
FIG. 5B is a diagram illustrating a process for disposing a bite scanning model and a tooth scanning model within a predetermined distance gap.

In an embodiment, the data acquisition unit 100 may obtain the bite scanning model 20 and the tooth scanning model 30 generated using an optical scanner. The pre-registering unit 210 may dispose the bite scanning model 20 and the tooth scanning model 30 within a predetermined distance gap (S21). That is, the step S21 corresponds to the step S13. As shown in FIG. 5B, the pre-registering unit 210 is a preliminary registering step before accurately registering the bite scanning model 20 to the tooth scanning model 30, and may roughly register the bite scanning model 20 to the tooth scanning model 30 (S21).

Figure 5C:
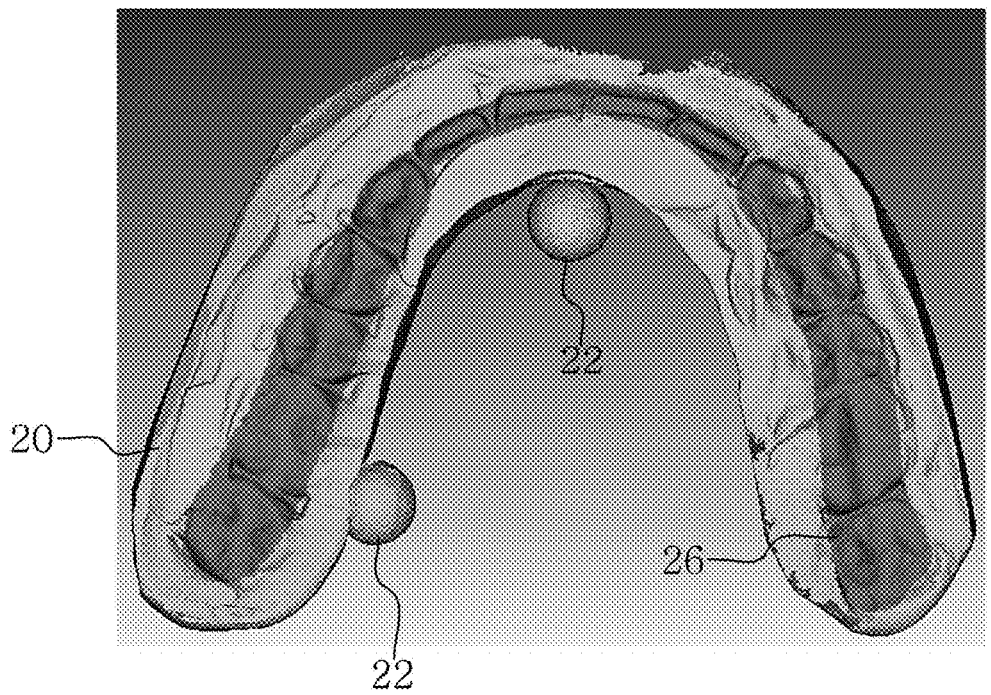
FIG. 5C is a diagram showing a third region of interest set on a bite scanning model.
Figure 5D:
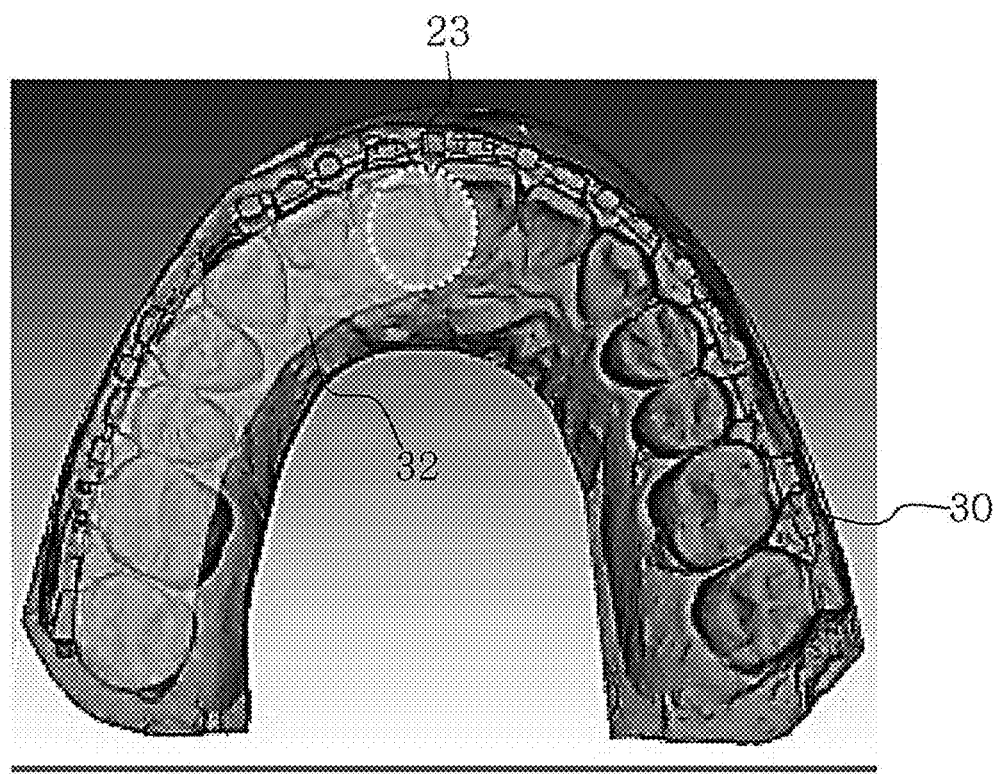
FIG. 5D is a diagram showing that a predetermined region is selected from a tooth scanning model by a user's input.
Figure 5E:
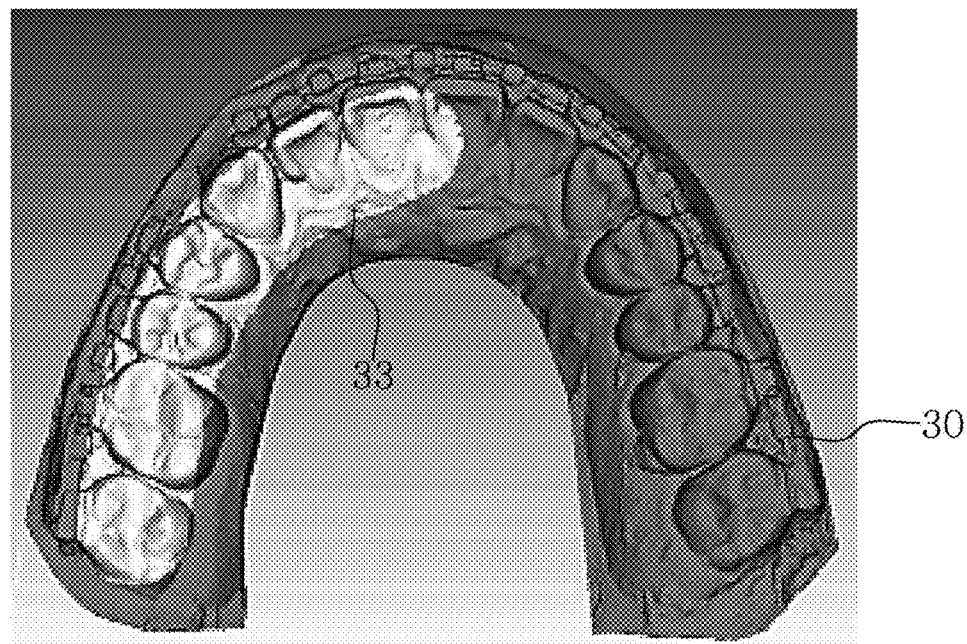
FIG. 5E is a diagram showing a fourth region of interest set on a tooth scanning model.
Figure 5F:
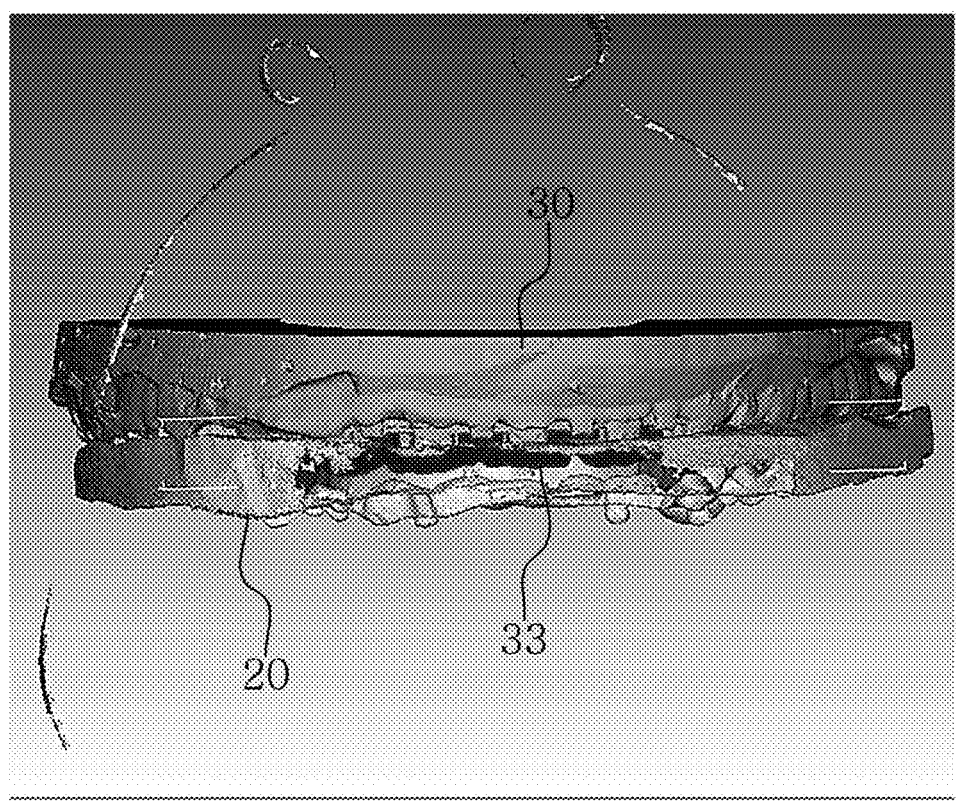
FIG. 5F is a diagram showing the second registering results according to an embodiment of the present disclosure.

In an embodiment, the second region of interest setting unit 500 may set a third region of interest and a fourth region of interest based on a predetermined region selected by the user input (S23 and S25). As shown in FIG. 5C, when a sunken part 21 of the tooth structure generated with the object biting the bite is selected 26 by the user, the second region of interest setting unit 500 may set the predetermined region 26 selected by the user, included in the obtained bite scanning model, as a third region of interest 26 (S23). As shown in FIG. 5D, when a part of the tooth structure 31 of the object corresponding to the sunken tooth structure 21 of the bite scanning model is selected 32 by the user, the second region of interest setting unit 500 may set the predetermined region 32 selected by the user, included in the obtained tooth scanning model, as a fourth region of interest 33 (S25). Methods for setting the third region of interest and the fourth region of interest use a method for setting the second region of interest, and to avoid complications, their description is omitted herein. In an embodiment, the set third region of interest and fourth region of interest may be displayed to the user through the display unit 600.

The main registering unit 220 may register the third region of interest 26 of the bite scanning model 20 with the fourth region of interest 33 of the tooth scanning model 30 through ICP algorithm (S27). In an embodiment, the main registering unit 220 may move the bite scanning model 20 so that an average of distances between reference points or all vertices that make up the fourth region of interest 33 and the third region of interest 26 is minimum using ICP algorithm (S27). In an embodiment, the main registering unit 220 may move the bite scanning model 20 so that an average of distances between reference points of the fourth region of interest 33 and references point of the third region of interest 26 corresponding to the reference points included in the fourth region of interest is minimum. In another embodiment, the main registering unit 220 may move the bite scanning model 20 so that an average of distances between all vertices that make up the fourth region of interest 25 and the third region of interest 26 is minimum.

Figure 6:
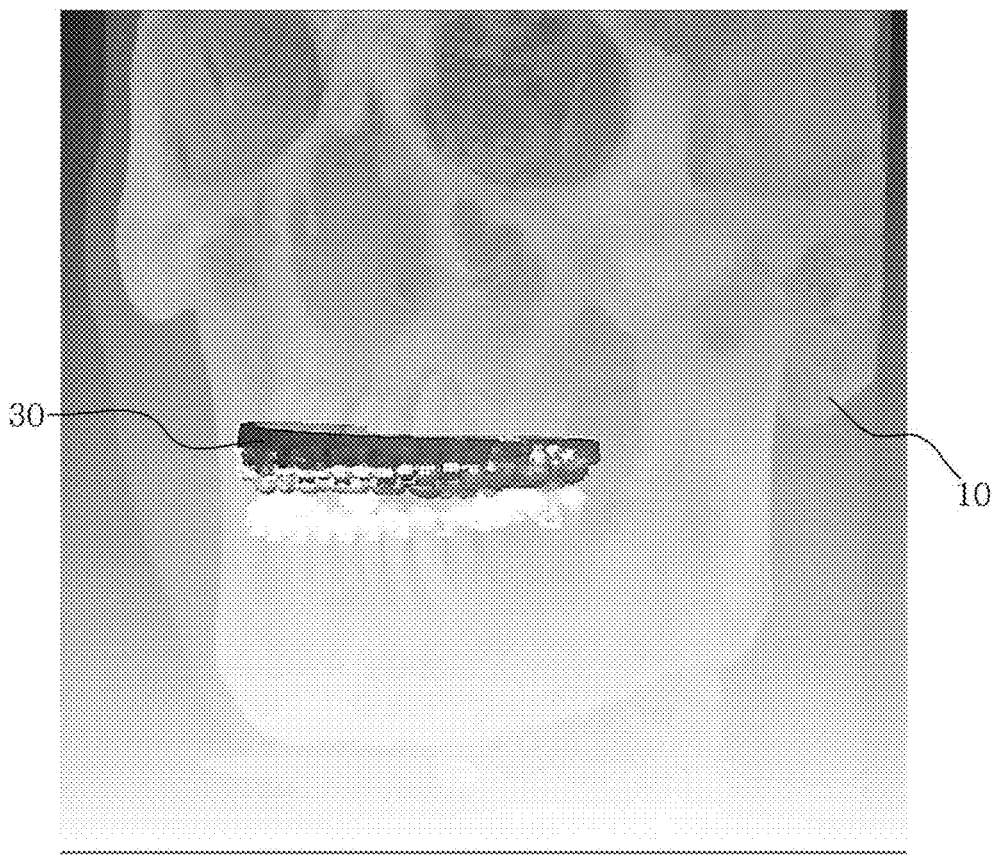
FIG. 6 is a diagram showing an image obtained by registering a tooth scanning model to a tooth image based on first and second registering results according to an embodiment of the present disclosure.

As a result, as shown in FIG. 6, the registering unit 200 may register the entire bite scanning model to the entire tooth scanning model.

The step of registering the bite scanning model to the tooth scanning model (S27) is considerably similar to the step of registering the tooth image model to the bite scanning model (S17) as described previously, and to avoid complications, its description is omitted herein.

The registering unit 200 may register the tooth image model to the tooth scanning model, based on the results of the first registering step and the results of the second registering step (S3). In an embodiment, as a result of registering at the second registering step, the coordinates of the structure of the tooth scanning model 30 may be calculated based on the bite scanning model 20. As a result of registering at the first registering step, the coordinates of the structure of the tooth image model 30 may be also calculated based on the bite scanning model 20. As a result, as shown in FIG. 6, based on the bite scanning model 20, the tooth image model may be registered to the tooth scanning model obtained by directly scanning the tooth structure of the object that is more accurate than the tooth shape of the object obtained from the medical imaging apparatus or the tooth structure of the object obtained from the object biting the bite. In another embodiment, the coordinates of the structure of the bite scanning model 20 may be calculated based on the tooth scanning model 30.

The order of the method for registering the tooth image to the tooth structure may be modified.

In another embodiment, the method for registering the tooth image to the tooth structure may be performed in an order of the second registering step (S2) and the first registering step (S1).

In still another embodiment, at the second registering step, the step of setting the third region of interest (S23) and the step of setting the fourth region of interest (S25) may be performed first, and the step of roughly registering the bite scanning model to the tooth scanning model (S21) may be performed.

As described above, the method for selective registering 3D radiography tooth image data with an optical scanning tooth model may be implemented as an application or in the form of program command that is executed through various computer components and may be recorded in a computer-readable recording medium. The computer-readable recording medium may include program command, data file and data structure singly or in combination. The program command recorded in the computer-readable recording medium may be specially designed and configured for the present disclosure, and may be known and available to those having ordinary skill in the field of computer software.

While the preferred embodiments have been hereinabove illustrated and described, the disclosure is not limited to the particular embodiments described above, various modifications may be made thereto by those having ordinary skill in the technical field to which the disclosure belongs, without departing from the subject matter of the appended claims, and these modifications should not be understood separately from the technical spirit or scope of the disclosure.

Furthermore, both a product invention and a method invention are described in the disclosure, and the description of the two inventions may be complementally applied when needed.

What is claimed is:

1. A method for registering a tooth image to a tooth structure, comprising:
    a first registering step for registering a tooth image model obtained from a medical image taken when an object bites a bite including a marker to a bite scanning model obtained by scanning the bite;
    a second registering step for registering the bite scanning model to a tooth scanning model obtained by scanning a tooth structure of the object; and
    a third registering step for registering the tooth image model to the tooth scanning model based on the results of the first registering step and the results of the second registering step.

2. The method for registering a tooth image to a tooth structure according to claim 1, wherein the bite scanning model or the tooth scanning model is obtained from an image generated using an optical scanner.

3. The method for registering a tooth image to a tooth structure according to claim 2, wherein the first registering step further comprises:
    setting the marker included in the tooth image model as a first region of interest;
    disposing the bite scanning model and the tooth image model within a predetermined distance gap based on the marker included in the bite scanning model and the first region of interest;
    setting the marker included in the bite scanning model as a second region of interest; and
    moving the tooth image model or the bite scanning model so that an average of distances between at least one reference point of the first region of interest and at least one reference point of the second region of interest corresponding to the at least one reference point of the first region of interest is minimum.

4. The method for registering a tooth image to a tooth structure according to claim 3, wherein the setting of the marker included in the tooth image model as the first region of interest comprises:
    displaying at least one of the marker included in the tooth image model, a tooth part and a structure installed at the tooth, based on a preset Hounsfield Unit (HU) value;
    determining a position of the marker by an user input for the displayed marker; and
    setting a region within a predetermined range based on a radius value of the marker as the first region of interest, based on the determined position of the marker.

5. The method for registering a tooth image to a tooth structure according to claim 3, wherein the setting of the marker included in the bite scanning model as the second region of interest further comprises:
    setting a start triangle at a start point of an user input for the bite scanning model within a predetermined region selected through the user input for the bite scanning model;

searching for a neighboring triangle sharing at least one of three vertices of the start triangle based on the start triangle;

iteratively searching for another neighboring triangle sharing at least one of three vertices of the neighboring triangle based on the neighboring triangle; and setting a region covered with the start triangle and the multiple found neighboring triangles in the bite scanning model as the second region of interest.

6. The method for registering a tooth image to a tooth structure according to claim 5, wherein the searching for the neighboring triangle comprises, when at least one of three vertices of any one found neighboring triangle is outside of the region selected through the user input for the bite scanning model, stopping searching for another neighboring triangle sharing one of three vertices of the neighboring triangle.

7. The method for registering a tooth image to a tooth structure according to claim 1, wherein the second registering step comprises:

disposing the bite scanning model and the tooth scanning model with a predetermined distance gap;

setting the tooth part included in the bite scanning model as a third region of interest;

setting the tooth part included in the tooth scanning model as a fourth region of interest; and moving the bite scanning model or the tooth scanning model so that an average of distances between at least one reference point of the third region of interest and at least one reference point of the fourth region of interest respectively corresponding to the at least one reference point of the third region of interest is minimum.

8. The method for registering a tooth image to a tooth structure according to claim 7, wherein the setting of the tooth part included in the bite scanning model as the third region of interest comprises:

setting a start triangle at a start point of the user input for the bite scanning model in a predetermined region selected through the user input for the bite scanning model;

searching for a neighboring triangle sharing at least one of three vertices of the start triangle based on the start triangle;

iteratively searching for another neighboring triangle sharing at least one of three vertices of the neighboring triangle based on the neighboring triangle; and setting a region covered with the start triangle and the multiple found neighboring triangles in the bite scanning model as the third region of interest, wherein the setting of the tooth part included in the tooth scanning model as the fourth region of interest comprises:

setting a start triangle at a start point of the user input for the tooth scanning model in a predetermined region selected through the user input for the tooth scanning model;

searching for a neighboring triangle sharing at least one of three vertices of the start triangle based on the start triangle;

iteratively searching for another neighboring triangle sharing at least one of three vertices of the neighboring triangle based on the neighboring triangle; and setting a region covered with the start triangle and the multiple found neighboring triangles in the tooth scanning model as the fourth region of interest.

9. The method for registering a tooth image to a tooth structure according to claim 8, wherein the searching for the neighboring triangle comprises, when at least one of three vertices of any one found neighboring triangle is outside of the region selected through the user input, stopping searching for another neighboring triangle sharing one of three vertices of the neighboring triangle.

10. The method for registering a tooth image to a tooth structure according to claim 1, wherein the third registering step comprises registering the tooth image model to the tooth scanning model using a coordinates result value of the first registering step and a coordinates result value of the second registering step.

11. The method for registering a tooth image to a tooth structure according to claim 1, wherein the tooth image model is generated based on the tooth image taken using at least one of Computed Tomography (CT), Cone-Beam Computed Tomography (CBCT), Magnetic Resonance Imaging (MRI), and X-ray.

12. An apparatus for registering a tooth image to a tooth structure, comprising:

a data acquisition unit configured to obtain a tooth image model generated from a tooth image taken when an object bites a bite including a marker, a bite scanning model generated by scanning the bite, and a tooth scanning model generated by scanning a tooth structure of the object;

a display unit;

a first region of interest model setting unit configured to set the marker included in the tooth image model as a first region of interest;

a second region of interest setting unit configured to set the marker included in the bite scanning model as a second region of interest, set the tooth part included in the bite scanning model as a third region of interest, and set the tooth part included in the tooth scanning model as a fourth region of interest;

a pre-registering unit configured to perform the step of registering within a predetermined distance gap by rotary movement or position movement of at least one of the tooth image model, the bite scanning model and the tooth scanning model; and a main registering unit configured to move at least one of the tooth image model, the bite image model and the tooth scanning model so that for two regions of interest of the set first, second, third and fourth regions of interest, an average of distances between at least one reference point of the two regions of interest is minimum respectively.

13. A computer program stored in a nontransitory computer-readable recording medium to perform a process in combination with hardware, the process comprising:

a first registering step for registering a tooth image model obtained from a medical image taken when an object bites a bite including a marker to a bite scanning model obtained by scanning the bite;

a second registering step for registering the bite scanning model to a tooth scanning model obtained by scanning a tooth structure of the object; and a third registering step for registering the tooth image model to the tooth scanning model based on the results of the first registering step and the results of the second registering step.

* * * * *